United States Patent [19]

Konteatis et al.

[11] Patent Number: 5,190,924

[45] Date of Patent: Mar. 2, 1993

[54] PEPTIDE AMIDES AND AMIDE DIMERS USEFUL AS MUSCLE RELAXANTS

[75] Inventors: Zenon D. Konteatis, Maplewood, N.J.; David C. Palmer, Bethlehem, Pa.

[73] Assignee: BOC Health Care, Inc., Murray Hill, N.J.

[21] Appl. No.: 654,736

[22] Filed: Feb. 13, 1991

[51] Int. Cl.$^5$ ............... A61K 37/00; A61K 37/02
[52] U.S. Cl. .................. 514/19; 514/18; 514/906; 530/330; 530/331; 530/323
[58] Field of Search ............ 514/19, 18, 906; 530/330, 331, 323

[56] References Cited

U.S. PATENT DOCUMENTS

| | | | |
|---|---|---|---|
| 4,018,912 | 4/1977 | Failli et al. | 514/18 |
| 4,320,051 | 3/1982 | Sarantakis | 514/18 |
| 4,468,383 | 8/1984 | Rodbard et al. | 514/18 |
| 4,476,117 | 10/1984 | Morley | 530/323 |
| 4,623,715 | 11/1986 | Geiger et al. | 530/330 |
| 4,812,442 | 3/1989 | Boger et al. | 514/18 |

OTHER PUBLICATIONS

Paton et al. *Pharmacological Reviews*, vol. 4, (1952), pp. 219–253.
Thornber et al. NIDA Res. Monograph, 75 (Prog. Opioid Res.), (1986) pp. 181–184.
Marr-Leisy et al., *Int. J. Peptide Protein Res.*, 25, (1985), pp. 290–296.

*Primary Examiner*—Ronald W. Griffin
*Attorney, Agent, or Firm*—R. Hain Swope; Larry R. Cassett

[57] ABSTRACT

Peptide amide and amide dimer muscle relaxants represented by the formulae:

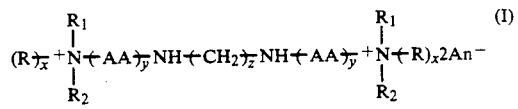

and

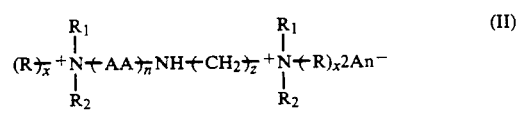

wherein: R is lower alkyl; $R_1$ and $R_2$ independently selected from the group consisting of hydrogen, lower alkyl, allyl, propargyl, aryl lower alkyl and cyclo-lower alkyl lower alkyl, or R plus one or both of $R_1$ and $R_2$, together with the nitrogen to which they are attached, form a heterocyclic ring having 5 to 7 member atoms; AA are independently selected from certain amino acids moieties; n is 2 to 4; x is independently 0 or 1; y is independently 1 or 2; z is 2 to 12; and $An^-$ is a pharmaceutically acceptable anion.

13 Claims, No Drawings

PEPTIDE AMIDES AND AMIDE DIMERS USEFUL AS MUSCLE RELAXANTS

This invention relates to certain peptide amides and amide dimers useful as nondepolarizing muscle relaxants.

BACKGROUND OF THE INVENTION

The neuromuscular action of certain compounds falling within the series $$Me_3N^+ - (CH_2)_n - N^+Me_3$$

has been reported in the literature. The muscle relaxant activity of two compounds in this series, decamethonium and hexamethonium, is discussed by Paton and Zaimis in *Pharmacological Reviews*. Vol. 4, (1952), pp 219-253. They observed that decamethonium closely imitated acetylcholine at the neuromuscular junction in certain species tested. By this mechanism of action, decamethonium is classified as a depolarizing type of muscle relaxant. This type of activity is sustained for as long as an effective concentration of the therapeutic agent remains at the receptor site.

Paton and Zaimis further observed that, as the length of the chain between the quaternary nitrogens in decamethonium is shortened, the depolarizing neuromuscular activity was reduced to negligible level. They found that d-tubocurarine acts on post-ganglionic structures and actually antagonizes acetylcholine. It is, therefore, a nondepolarizing muscle relaxant.

There is neither teaching nor suggestion in Paton and Zaimis that a diamine having a polypeptide chain separating quaternary nitrogens would be useful as a muscle relaxant of any type. There is nothing in Paton and Zaimis that would suggest that, were such compounds synthesized, they would have any therapeutic activity.

Thornber et al. *NIDA Res. Monograph*, 75 (*Prog. Opioid Res*), 181, (1986) describe the preparation of dimeric pentapeptides by the addition of amino acid moieties to the amino groups of ethylene diamine.

Boger et al., U.S. Patent No. 4,812.442, disclose enzyme tripeptides of the general formula:

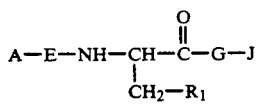

wherein the designations A,E,G,J and $R_1$ have a broad variation of meanings. The disclosed peptides can contain only one quaternary amino moiety. They are useful in treating various forms of renin-associated hypertension.

In accordance with the present invention, it has been found that certain peptide amides and amide dimers possess significant nondepolarizing muscle relaxant activity, thus making them useful therapeutically as skeletal muscle relaxants.

SUMMARY OF THE INVENTION

The present invention pertains to certain novel peptide amides and amide dimers pharmaceutical compositions containing them and the use thereof to produce a muscle relaxant effect in mammals.

DETAILED DESCRIPTION OF THE INVENTION

The peptide amides and amide dimers of the subject invention are selected from those represented by the formulae:

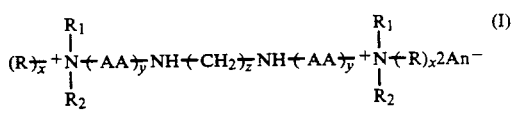

and

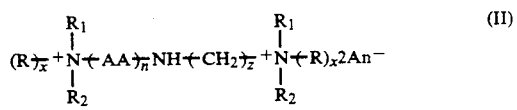

wherein
R is lower alkyl;
$R_1$ and $R_2$ are independently selected from the group consisting of hydrogen, lower alkyl, allyl, propargyl, aryl lower alkyl and cyclo-lower alkyl lower alkyl, or R plus one or both of $R_1$ and $R_2$ together with the nitrogen to which they are attached form a heterocyclic ring having 4 to 6 member atoms;
AA are independently selected from the group consisting of Ala, Val, Leu, Ile, Phe, Tyr, Pro, Nip, 4-AcOPro, Glu(γ-Me), GABA and 6-amino hexanoic acid;
n is 2 to 4;
x is independently 0 or 1;
y is independently 1 or 2;
z is 2 to 12, and
$An^-$ is a pharmaceutically acceptable anion.

In accordance with the present invention, the term "lower alkyl" is a branched- or unbranched-hydrocarbon radical containing from 1 to 7 carbon atoms. Preferred lower alkyl groups in accordance with the subject invention are methyl and ethyl. The term "cyclolower alkyl", as utilized herein, means cyclic alkyl groups containing from 3 to 6 carbon atoms. The term "aryl" as utilized herein is intended to mean phenyl or naphthyl which may be unsubstituted or substituted with up to three substituents selected from the group and consisting of halogen, halogenated lower alkyl, lower alkyl, hydroxy and lower alkoxy. Preferred aryl groups include phenyl, 1-naphthyl and 2-naphthyl.

The pharmaceutically acceptable anions represented by the $An^-$ in the above formulae include, for example, inorganic anions such as the chloride, bromide, sulfate, phosphate and the like, and organic anions such as the acetate, oxalate, trifluoroacetate, benzene sulfonate, succinate, tartrate, citrate and the like. Prefereed anions include the chloride, the trifluoroacetate, the iodide, and the benzene sulfonate.

The amino acids and amino acid esters represented by "AA" in the above formulae will be referred to herein by their conventional abbreviations for the sake of brevity. Such abbreviations are well known to those skilled in the art. The primary abbreviations are given below:

| | | | |
|---|---|---|---|
| Alanine | Ala | Valine | Val |
| Leucine | Leu | Isoleucine | Ile |
| Phenylalanine | Phe | Tryptophan | Trp |
| Tyrosine | Tyr | Nipecotic Acid | Nip |
| Glutamic Acid | Glu | | |
| 4-Acetoxyproline | 4-AcOPro | | |

| | -continued |
|---|---|
| Tetrahydro-isoquinoline Carboxylic Acid | Tic |
| Glutamic Acid Gamma Methyl Ester | Glu(γ-Me) |
| 1- and 2-Naphthylalanine | 1- and 2-Naphthala |
| Gamma-aminobutyric acid | GABA |

Unless it is specified herein that the amino acid moieties which make up the subject peptide amide and amide dimers are in the D-form or the L-form, both forms are intended.

Preferred compounds within the scope of the present invention are those in the above formulae wherein $R_1$ and $R_2$ are independently selected from the group consisting of methyl, ethyl, allyl, benzyl and cyclopropylmethyl. Wherein R, $R_1$ and/or $R_2$, together with the nitrogen to which they are attached, form a 5- to 7-member heterocyclic ring, such rings may contain additional hetero atoms, i.e. N, O or S. Examples of suitable heterocyclic rings include pyrrolidine, piperidine, hexamethyleneimine, morpholine, piperazine and the like.

A particularly preferred group of compounds within the scope of the present invention are those of the above formulae wherein $R_1$ and $R_2$ are independently selected from the group consisting of methyl, ethyl and allyl, or R, $R_1$ and/or $R_2$, together with the nitrogen to which they are attached, form a 5- to 7-member heterocyclic ring, the amino acids (AA) are independently selected from the group consisting of Ala, Leu, Phe, 1-Naphthala and 2-Naphthala, and z is 3–12.

Still another preferred group of muscle relaxants within the scope of the present invention are compounds of formula II above wherein R is methyl or ethyl, $R_1$ and $R_2$ are independently selected from the group consisting of methyl, ethyl and allyl, or R, $R_1$ and $R_2$, together with the nitrogen to which they are attached, form a heterocyclic ring selected from the group consisting of pyrrolidine, piperidine, piperazine, and hexamethyleneimine, the amino acids are independently selected from the group consisting of Ala, Leu, Phe, 1-Naphthala and 2-Naphthala, and z is 3–12. Specific preferred peptide amide and amide dimers within the preceding groups are the following:

$Me_3N^+$-Phe-NH-$(CH_2)_3$-NH-Phe-$N^{30}Me_3$2An$^-$
$Me_3N^+$-Phe-NH-$(CH_2)_4$-NH-Phe-$N^{30}Me_3$2An$^-$
$Me_3N^+$-Phe-NH-$(CH_2)_5$-NH-Phe-$N^{30}Me_3$2An$^-$
$Me_3N^+$-Phe-NH-$(CH_2)_6$-NH-Phe-$N^{30}Me_3$2An$^-$
$Me_3N^+$-Phe-NH-$(CH_2)_7$-NH-Phe-$N^{30}Me_3$2An$^-$
$Me_3N^+$-Phe-NH-$(CH_2)_8$-NH-Phe-$N^{30}Me_3$2An$^-$
$Me_3N^+$-Phe-NH-$(CH_2)_{10}$-NH-Phe-$N^{30}Me_3$2An$^-$
$Me_3N^+$-Phe-NH-$(CH_2)_{12}$-NH-Phe-$N^{30}Me_3$2An$^-$
$Me_3N^+$-D-Phe-NH-$(CH_2)_5$-NH-D-Phe-$N^+Me_3$2An$^-$
α-[Me-$N^+(CH_2)_5$]-Phe-NH-$(CH_2)_5$-NH-Phe-α-[Me-$N^+(CH_2)_5$2]An$^-$
$Me_3N^+$-Ala-NH-$(CH_2)_6$-NH-Ala-$N^+Me_3$2An$^-$
$Me_3N^+$-2-Naphthala-NH-$(CH_2)_6$-NH-2-Naphthala-$N^+Me_3$2An$^-$
$Me_3N^+$-Phe-Leu-NH-$(CH_2)_2$-$N^+Me_3$2An$^-$
$Me_3N^+$-Phe-Leu-NH-$(CH_2)_6$-$NMe^+_3$2An$^-$
$Me_3N^+$-Phe-Leu-NH-$(CH_2)_7$-$N^+Me_3$2An$^-$
$Me_3N^+$-D-Phe-D-Leu-NH-$(CH_2)_6$-$N^+Me_3$2An$^-$
$Me_3N^+$-Leu-Phe-Leu-NH-$(CH_2)_5$-$N^+Me_3$2An$^-$
$Me_3N^+$-Leu-Phe-Leu-NH-$(CH_2)_6$-$N^+Me_3$2An$^-$
$Me_3N^+$-Leu-Phe-Leu-NH-$(CH_2)_7$-$N^+Me_3$3An$^-$ The compounds of the present invention can be prepared by various methods.

Generally, the polypeptide skeletal muscle relaxants of the present invention may be prepared by solution phase peptide synthetic procedures analogous to those described hereinafter or methods known to those skilled in the art. For example, carboxylic moieties such as N-α-carbobenzyloxy (Cbz), N-α-fluorenylmethyloxycarbonyl(Fmoc), and N-α-t-butyloxycarbonyl( Boc) or substituted amino acid derivatives having suitable side chain protecting groups, if necessary, may be condensed with the amino functionality of a suitably protected amino acid or peptide using conventional coupling protocols such as dicyclohexylcarbodiimide (DCC), N-diethylaminopropyl-N'-cyclohexylcarbodiimide (EDCC) or 1-hydroxybenzotriazole (HOBt) in methylene chloride or dimethylformamide. Such coupling reactions are described, for example, in Meienhofer-Gross, *The Peptides*, Academic Press, Vol. 1, (1979) or Bodanszky-Bodanszky, *The Practice of Peptide Synthesis*, Springer-Verlag, (1984).

Following coupling reaction completion, the protectant moieties are removed as follows. The N-α-Boc moiety may be selectively removed with 50% trifluoroacetic acid (v/v) in methylene chloride. Neutralization of the resultant trifluoroacetate salt may be accomplished with a slight excess of triethylamine or diisopropylethylamine in methylene chloride. In the case of the N-α-Cbz moiety, selective removal is accomplished using hydrogen gas and a catalyst such as 5–10% palladium on carbon in a lower alkanol solvent such as methanol, ethanol or 2-propanol. Selective N-α-Fmoc moiety may be accomplished using 20% piperidine (v/v) in methylene chloride.

According to a further feature of the invention, there is provided a process for the manufacture of those of the compounds of the formulae I and II which contain the groups:

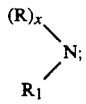

where x=1 and $R_1$ and $R_2$ are independently selected from the group consisting of lower alkyl, aryl lower alkyl and cyclo-lower alkyl lower alkyl, and pharmaceutically acceptable salts thereof which comprises reacting the corresponding compound containing the group $NH_2$—$(AA)_y$— or $NH_2$—$(AA)_n$—, generated either in situ by conventional deblocking methodology or from an isolated intermediate by reaction with the appropriate aldehyde or ketone and an alkali metal hydride reducing agent or hydrogen gas and a catalyst such as 5–10% palladium on carbon. The aldehyde or ketone may be, for example, formaldehyde, acetaldehyde, benzaldehyde, cyclopropane carboxaldehyde, glutaraldehyde, or acetone. The alkali metal hydride may be, for example, an alkali metal borohydride such as sodium cyanoborohydride. The process is conveniently carried out in methanol, optionally together with acetic acid or 1-hydroxyethylpiperazine ethanesulfonic acid (HEPES), at ambient temperature. The methods mentioned are described, for example, in Gormley, U.S. Pat. No. 4,421,744 (1983).

According to a further feature of the invention, there is provided a process for the manufacture of those of the compounds of the formula I which contain the groups:

where x=1; R is lower alkyl and $R_1$ and $R_2$ are independently selected from the group consisting of lower alkyl, allyl, propargyl, aryl lower alkyl and cyclo-lower alkyl lower alkyl or R plus one or both of $R_1$ and $R_2$, together with the nitrogen to which they are attached, form a heterocyclic ring having 5 to 7 member atoms, and pharmaceutically acceptable salts thereof which comprises reacting a compound containing the group:

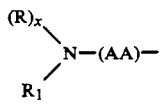

with a compound of the formula $R_2Hal$ wherein $R_2$ has the meaning stated above and Hal stands for a halogen atom. Suitable solvents for this alkylation reaction include methanol, ethanol, acetonitrile and dimethylformamide.

A compound containing the group $NH_2$—(AA)— may be reacted with a compound of the formula $R_1Hal$ or $R_2Hal$ wherein $R_1$, and $R_2$ and Hal have the meanings stated above, in the presence of an acid-binding agent. A suitable acid-binding agent is, for example, an alkali metal carbonate or bicarbonate such as potassium carbonate or sodium bicarbonate. The process is conveniently carried out in methanol, ethanol, acetonitrile or dimethylformamide. This method is described, for example, in Benoiton-Chen, *Proced, 14th Europ. Pept. Symp.*, (1976), p. 149.

The compounds of the present invention are formulated with a pharmaceutically acceptable carrier to provide a pharmaceutical composition for parenteral, i.e. intravenous, intramuscular or subcutaneous. administration. Suitable carriers include isotonic water, sterile water for injection (USP), alone or in combination with other solubilizing agents such as ethanol, propylene glycol, or other conventional solubilizing agents known to those skilled in the art. A preferred carrier is an isotonic aqueous solution.

Sterile solutions or suspensions of the compounds of the present invention preferably contain at least about 0.1% by weight of the active compound, but this amount may be varied to as much as about 50% by weight. The exact amount of the subject compound present in such compositions is such that a suitable dosage level will be obtained. Preferred compositions and preparations according to the present invention are prepared so that a parenteral dosage unit contains from between about 150 to about 1000 milligrams of the compound of formula I.

The sterile solutions or suspensions prepared in accordance with the subject invention may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite, chelating agents such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dose vials made of glass or plastic.

The compounds of the present invention can be administered to mammals, e.g; animals or humans, in amounts effective to provide the desired muscle relaxant therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitivity of the particular patient. Thus, the unit dosage for a particular patient (man) can be as low as about 2 mg/kg, which the practitioner may titrate to the desired effect.

The peptide amides and amide dimers of the present invention are skeletal muscle relaxants of the competitive or nondepolarizing type (curariform). This type of muscle relaxant is preferred over the depolarizing agents, such as succinylcholine chloride, because of greater control. Nondepolarizing skeletal muscle relaxants antagonize the neurotransmitter action of acetylcholine by binding competitively with cholinergic receptor plates on the motor end plate. Most known nondepolarizing skeletal muscle relaxants, such as pancuronium bromide, cetacurium besylate and vecuronium bromide, have an intermediate duration of therapeutic activity. The subject compounds are advantageous in comparison therewith since, in addition to having a very rapid onset of action, they possess a short duration of activity. These properties are particularly useful as an adjunct to general anesthesia. The preferred peptide amides of the present invention are useful to facilitate short medical procedures such as endotrachial intubation, and for skeletal muscle relaxation during surgery or mechanical ventilation. These therapeutic indications are considered to be unexpected since, to Applicants' knowledge, there are no other peptide amides possessing this type of activity.

The following Examples illustrate this invention, it being understood that the invention is in no way intended to be limited to the details described therein. In the Examples, all parts and percentages are on a weight basis and all temperatures are in degrees Celsius, unless otherwise stated.

EXAMPLE 1

Diiodide salt of bis-(N,N,N-trimethyl-L-phenylalanyl) -decane-1,10-diamide

To a stirred suspension of 1,10-diaminodecane (0.862 g; 5 mmol), triethylamine (1.4 ml, 10.1 mmol) and 1-hydroxybenzotriazole (0.383 g; 2.5 mmol) in methylene chloride (100 ml) was added N-α-benzyloxycarbonyl-L-phenylalanine para-nitrophenyl ester (4.2 g; 10 mmol), and the resulting yellow solution was stirred overnight. The white precipitate was filtered and washed successively with methylene chloride, 5% $Na_2CO_3$ and diethylether. Bis-(N-α-benzyloxycarbonyl-L-phenylalanyl)-1,10-diaminodecane was isolated as a white solid (2.6 g., 3.66 mmol) with $R_t=27.4$ min.

A suspension of the above product (2.55 g; 3.47 mmol), 10% Pd/C (1.0 g.) and 37% aqueous formaldehyde (5 ml, 66.5 mmol) in methanol (50 ml) and glacial acetic acid (50 ml) was placed in a Parr hydrogenation apparatus, flushed with $N_2$ and then charged with $H_2$ (50 psi) for 12 hours. The resulting mixture was filtered through celite to remove the catalyst. The filtrate was concentrated in vacuo to leave a yellow-orange oil which was dissolved in methylene chloride (50 ml) and washed with 5% Na$_2$CO$_3$. The methylene chloride solution was dried over MgSO$_4$ and evaporated in vacuo to leave a pale yellow oil which was dissolved in diethylether and evaporated in vacuo to yield bis-(N,N-dimethyl-L-phenylalanyl) -1,10-diaminodecane as a white precipitate (1.474 g.), R$_t$=18.03 min.

The product was characterized by IR, NMR and MS. The fast atom bombardment (FAB) MS showed (M+H)$^+$ at m/z calc'd: 522.8. Found: 523. Anal. calc'd for: C$_{32}$N$_{50}$N$_4$O$_2$: C, 73.52; H, 9.64; N, 10.72. Found: C, 73.58; H, 9.53; N, 10.52.

A solution of the above product (0.3 g; 1.71 mmol) in methanol (30 ml) was treated with methyliodide (1 ml, 16.1 mmol), and the resulting solution stirred at ambient temperature for 24 hours. The methanol was removed in vacuo and the resulting white precipitate redissolved in methanol which was again removed in vacuo to leave a white solid. This was washed with diethyl ether which was evaporated in vacuo to leave bis-(N,N,N-trimethyl-L-phenylalanyl) -decane-1,10-diamide diiodide, as a yellow solid (1.66 g.) R$_t$=18.64 min.

The product was characterized by IR, NMR and MS. The fast atom bombardment (FAB) MS showed (M+I$^-$)$^+$ calc'd: 679.8. Found 680. Anal. calc'd for C$_{34}$H$_{56}$N$_4$O$_2$×2 I$^-$: C, 50.63; H, 7.00; N, 6.95. Found: C, 50.37; H, 7.03; N, 6.73.

EXAMPLE 2

Tetrakis-trifluoroacetate salt of N,N,N-trimethyl-L-phenylalanyl-L-leucine-(7-trimethylammonium) heptylamidene A suspension of N-α-t-butoxycarbonyl-L-phenylalanine (5.306 g., 20.0 mmol), L-leucine methyl ester hydrochloride (3.634 g; 20.0 mmol) and 1-hydroxybenzotriazole (3.069., 20.0 mmol) in dimethylformamide (50 ml) and methylene chloride (100 ml) was stirred and cooled to 0° in an ice bath. Triethylamine (2.8 ml, 20.1 mmol) was added followed by 1-ethyl-3-(3-dimethylaminopropyl)carbodiimide hydrochloride (3.856 g., 20.2 mmol) and the resulting pale yellow solution was stirred overnight during which time it slowly warmed to ambient temperature. The solution was evaporated in vacuo and the residue re-dissolved in methylene chloride (150 ml) and washed successively with 5% NaHCO$_3$, water and saturated brine. The methylene chloride was dried over MgSO$_4$. Evaporation gave a pale yellow solid which was suspended in heptane and filtered. The product, N-α-t-butoxycarbonyl-L-phenylalanyl-L-leucine methyl ester 6.52 g. was isolated as a white solid with mp 99°-101° and R$_t$=23.7 min.

A solution of the above product (7.94 g; 20.23 mmol) in methanol (100 ml) was treated with 10% NaOH (20 ml) and stirred at ambient temperature for 2 hours. RP-HPLC analysis of an aliquot at this time showed only product present. The reaction mixture was quenched with glacial acetic acid (20 ml) and was evaporated to leave a pasty wax which was suspended in water and filtered. The resulting white solid was washed liberally with water and dried in vacuo at 100° overnight. The product N-α-t-butoxycarbonyl-L-phenylalanyl-L-leucine weighed 7.510 g. and had mp 135°-9° and R$_t$=21.74 min.

A suspension of the above product (1.132 g; 2.99 mmol) and 1-hydroxybenzotriazole (0.475 g; 3.10 mmol) in methylene chloride (50 ml) was stirred, cooled to 0° and treated successively with 7-dimethylaminoheptylamine (0.505 g, 3.19 mmol) and dicyclohexylcarbodiimide (0.656 g; 3.18 mmol). The resulting colorless solution was stirred and allowed to warm to ambient temperature overnight. The precipitated dicyclohexyl urea was removed by filtration and washed with methylene chloride (50 ml). The combined methylene chloride washes and the filtrate were washed successively with 5% NaHCO$_3$, water and saturated brine. The methylene chloride was dried over MgSO$_4$ and evaporated in vacuo to obtain a pale yellow, pasty solid. Addition of diethyl ether (100 ml) and re-evaporation afforded the product N-α-t-butoxycarbonyl-L-phenylalanyl-L-leucine-(7-dimethylamino)-heptylamide as a pale yellow glass (R$_t$=20.81 min.) which was used without further purification in the deblocking reaction.

The above product was dissolved in methylene chloride (10 ml), treated with trifluoroacetic acid (10 ml) and stirred at ambient temperature for 1 hour. The methylene chloride and excess trifluoroacetic acid were evaporated in vacuo to leave a pale yellow syrup. Water (20 ml) was added, a small amount of insoluble material was removed by filtration and the aqueous filtrate lyophilized to afford L-phenylalanyl-L-leucine-(7-dimethylamino) heptylamide tri-trifluoroacetate as a hygroscopic solid with R$_t$=13.90 min.

The product was characterized by IR, NMR and MS. The fast atom bombardment (FAB) MS showed (M+H)$^+$ at m/z calc'd: 428.6. Found: 419 and (M+Na)$^+$ at m/z calc'd: 441.6. Found: 441. Anal. calc'd for C$_{24}$H$_{42}$N$_4$O$_2$×3 CF$_3$CO$_2$H×1.5 H$_2$O: C, 45.74; H, 6.14; N, 7.11. Found: C, 48.68; H, 6.11; N, 7.03.

A solution of the above product in methanol (25 ml) was treated with NaHCO$_3$ (1.663 g; 19.81 mmol) and methyl iodide (3.0 ml, 48.7 mmol) and the resulting suspension stirred at ambient temperature for 48 hours. The inorganic salts were removed by filtration and washed liberally with methanol. The methanol was removed in vacuo to leave a yellow syrup which was dissolved in water and lyophilized to give 2.054 g. of crude product. This was purified using RP-HPLC on a Vydac C-18 2 inch column; gradient system: Buffer A, 0.1% aqueous trifluoroacetic acid; Buffer B, acetonitrile, 0–100% in 30 min. with UV detection at 220 nm. Pooled fractions were lyophilized to give 1.010 g. of N,N,N-trimethyl-L-phenylalanyl-L-leucine-(7-trimethylammonium) heptylamidetetrakis-trifluoroacetate as a pale yellow syrup.

The product was characterized by IR, NMR and MS. The fast atom bombardment (FAB) MS shows (M+H)$^+$ at m/z calc'd: 476.7. Found: 477 and (M+TFA$^-$)$^+$ at m/z calc'd: 589.7. Found: 590. Anal. calc'd for C$_{28}$H$_{52}$N$_4$O$_2$×2C$_2$F$_3$O$_2^-$×2CF$_3$CO$_2$H: C, 46.45; H, 5.85; N, 6.01. Found: C, 46.50; H, 6.36: N, 6.26.

EXAMPLE 3

Bis-trifluoroacetate salt of N,N,N-trimethyl-L-leucyl-L-phenylalanyl-L-Leucine-(7-trimethylammonium) heptylamide A solution of N-α-t-butoxycarbonyl-L-phenylalanine (19.901 g.. 75.01 mmol), L-leucine benzyl ester tosylate (29.537 g., 75.06 mmol) and 1-hydroxybenzotriazole (11.93 g., 77.90 mmol) in a mixture of dimethylformamide (75 ml) and methylene chloride (325 ml) was stirred, cooled to 0° and treated with triethylamine (10.6 ml, 76.05 mmol), followed by dicyclohexylcarbodiimide (25.729 g., 76.23 mmol). The resulting pale yellow solution was stirred overnight during which time it warmed to ambient temperature. The dicyclohexylurea (DCU) was filtered out and washed with methylene chloride. The methylene chloride solution was washed sequentially with 5% NaOH, 5% HCl and saturated brine and then evaporated to leave a pale yellow syrup which was triturated with diethyl ether (250 ml). After filtration of additional DCU, evaporation of the diethyl ether afforded 28.04 g. of N-α-t-butoxycarbonyl-L-phenylalanyl-L-leucine benzyl ester as a white solid, $R_t = 27.19$ min.

A solution of the above product (15.965 g., 35.27 mmol) in methylene chloride (25 ml) was treated with trifluoroacetic acid (25 ml, 324.5 mmol) and stirred at ambient temperature for 80 min. The methylene chloride and excess trifluoroacetic acid were evaporated in vacuo to leave a viscous yellow syrup. The syrup was triturated with diethyl ether (100 ml) and the resulting pale yellow solid filtered and washed liberally with diethyl ether. There was obtained 14.453 g. white solid, m.p. 141°-4°, $R_t = 21.39$ min. which was used in the following reaction without further purification.

A solution of the above product (14.453 g., 30.98 mmol), 1-hydroxybenzotriazole (4.825 g., 31.51 mmol) and N-α-t-butoxycarbonyl-L-leucine (7.89 g., 31.66 mmol) in a mixture of dimethylformamide (25 ml) and methylene chloride (250 ml) was stirred, cooled to 0° and treated with triethylamine (4.50 ml, 32.29 mmol), followed by dicyclohexylcarbodiimide (6.551 g., 32.76 mmol). The resulting pale yellow solution was stirred overnight during which time it warmed to ambient temperature. The dicyclohexylurea (DCU) was removed by filtration and the methylene chloride and dimethyl formamide evaporated in vacuo to leave a syrupy solid. Diethyl ether (200 ml) was added and additional DCU removed by filtration. The filtrate was washed successively with 5% NaOH, 5% HCl, saturated brine and dried over MgSO$_4$. After filtration of the MgSO$_4$, evaporation of the diethyl ether gave N-α-t-butoxycarbonyl-L-leucyl-L-phenylalanyl-L-leucine benzyl ester as a pale yellow solid, $R_t = 28.60$ min. which was used without further purification.

A Parr bottle was charged with a solution of all of the above product in methanol (300 ml), and a suspension of 10% palladium on carbon (5.00 g.) in water (10 ml) was added thereto. The bottle was pressurized to 50 psi with hydrogen and shaken at ambient temperature for 16 hours. The catalyst was removed by filtration through a pad of celite and washed thoroughly with methanol (50 ml). Evaporation of the methanol in vacuo afforded a white foam which was converted to a white solid, N-α-t-butoxycarbonyl-L-leucyl-L-phenylalanyl-L-leucine, after 24 hours at 0.1 mm, 11.57 g. $R_t = 23.08$ min.

A solution of the above product (1.666 g., 3.12 mmol) and 1-hydroxybenzotriazole (0.502 g., 3.28 mmol) in a mixture of dimethylformamide (2 ml) and methylene chloride (60 ml) was stirred, cooled to 0°, and treated with 7-dimethylaminoheptylamine (0.517 g., 3.27 mmol), followed by dicyclohexlycarbodiimide (0.809 g., 3.33 mmol). The pale yellow solution was stirred overnight during which time it warmed to ambient temperature. The precipitated dicyclohexylurea (DCU) was removed by filtration and washed with methylene chloride (50 ml). The methylene chloride was washed successively with 5% NaOH and saturated brine and dried over MgSO$_4$. After filtration of the MgSO$_4$, evaporation of the methylene chloride afforded 1.74 g. of a pale yellow solid $R_t = 21.54$ min. which was used without further purification.

A solution of the above (1.74 g., 2.75 mmol) in methylene chloride (10 ml) was stirred and treated with trifluoroacetic acid (10 ml). The resulting pale yellow solution was stirred at ambient temperature for 75 min. The methylene chloride and excess trifluoroacetic acid were evaporated in vacuo and the residue treated with warm water (40 ml). Insoluble material was removed by filtration. Lyophilization afforded 1.668 g. of tri-trifluoroacetate salt of L-leucyl-L-phenylalanyl-L-leucine-(7-dimethylamino) heptylamide as a cream solid with $R_t = 15.68$ min. The product is characterized by IR, NMR and MS.

A solution of the above product (0.983 g., 1.22 mmol) in methanol (25 ml) was treated with NaHCO$_3$ (1.755 g., 20.89 mmol) and methyl iodide (3.0 ml, 48.19 mmol) and stirred overnight at ambient temperature. The inorganic salts were removed by filtration and washed with methanol (25 ml). Evaporation of the methanol afforded a pale yellow solid which was dissolved in warm water (30 ml) and filtered to remove a small amount of insoluble material. Lyophilization afforded crude N,N,N-trimethyl-L-leucyl-L-phenylalanyl-L-leucine-7-trimethylammonium heptylamide diiodide as a cream solid which was purified by RP-HPLC on a Vydac C-18 2 inch column using gradient system: Buffer A, 0.1% TFA/H$_2$O; Buffer B, acetonitrile, 0–100% in 30 min with UV detection at 220 nm. Pooled fractions were lyophilized to give 0.36 g. of product as the bis-trifluoroacetate in the form of a hygroscopic white solid, $R_t = 18.30$ min.

The product was characterized by IR and NMR. Anal. calc'd for $C_{34}H_{63}N_5O_3 \times 2CF_3CO_2^- \times 1.5CF_3CO_2H \times H_2O$: C, 49.03; H, 6.67; N, 6.97. Found: C, 49.39; H, 6.80; N, 7.12.

EXAMPLE 4

The following bioassay methodologies were used to demonstrate the neuromuscular junction blocking activity of the compounds of the invention. The relaxant properties of compounds with this pharmacologic mechanism could be used during surgical anesthesia to facilitate endotracheal intubation and retraction of muscle groups as required to expedite access to various body cavities. Each of these tests extended the knowledge of the clinical potential of the subject compounds. In stances where the compounds of this invention were not subjected to analysis in a specific test, it is possible to estimate such activity based on known relationships to other clinically available drugs which had been tested.

The first step, in mice, establishes a preliminary estimate of the potency and efficacy of the compounds. The animals were placed on a screen, inclined 45° to the horizontal. Effective doses caused the mice to lose their grip and slide down the inclined screen. The dose in mg/kg of body weight required to inhibit grip strength in 100% of the mice tested in a dosage group is reported.

The type of muscle relaxation produced by the test compounds was then determined by injection into chicks. Compounds which cause competitive blockage of post-synaptic acetylcholine receptors, i.e. nondepolarizing drugs, produce a flaccid paralysis in the chicks whereas drugs which cause depolarization of the post-synaptic muscle membrane produce a rigid paralysis. Only those compounds shown by this test to be nondepolarizing are tested further. This test established that the subject compounds are nondepolarizing muscle relaxants.

The rabbit paw twitch analysis was used to demonstrate the rate of onset and duration and to confirm the range of potency of test compounds. In a large series of similar telaxants, the rabbit dose is typically 125% of that in mice. The mechanism of action was also confirmed in this test by observing train-of-four and tetanus fade, post-tetanic potentiation of single twitches and administration of the anticholinesterase drug neostigmine which reverses the relaxation. Reversibility, rapid onset and short duration are important factors to the anesthesiologist.

In Table I, the doses of the compounds of the invention are shown relative to doses of clinically available drugs. Clinically, 0.1 to 0.14 mg/kg of vecuronium has been used for endotracheal intubation, while 0.010 mg/kg is used for maintenance of relaxation. Therefore, as an estimate of the range of possible dosages which might be employed for the subject compounds, the ED90 would be doubled as an estimate for an intubating dose, while a dose 20 to 25% of the ED90 dose might be required for maintenance bolus doses. The clinical dose range might be between 29% to 200% of the estimated ED90.

TABLE I

| Neuromuscular Junction Blocking Activity (ED90 in mg/kg) | | |
|---|---|---|
| Drug | Mouse | Rabbit |
| vercuronium | 0.025 | 0.020 |
| atracurium | 0.631 | 0.050 |
| Compound A | 7.940 | N/A |
| Compound B | 3.981 | N/A |
| Compound C | 1.259 | 4.408 |
| Compound D | 16.000 | 31.13 |
| Compound E | 1.995 | N/A |

The detailed pharmacologies in rabbits of two of the subject compounds are presented in Table II. The following is a brief description of the methodologies used in rabbits to describe neuromuscular blocking activity of the subject compounds. A more detailed description of these methods is presented in "Microcomputer Use in Measuring Onset, Duration, and Recovery from Non-Depolarizing Skeletal Muscle Relaxants in Rabbits", P. D. Thut et al, *Drug development Research* 5:182, 1985.

Male New Zealand white rabbits weighing between 2.5 and 3.4 kg were anesthetized with pentobarbital (30 mg/kg) and placed on their backs upon a 40° C. water filled temperature regulation pad. Following tracheostomy, the lungs were mechanically ventilated at 28 breaths per minute with room air, using an open system delivering 200 mi/stroke. This ventilation maintained pCO$_2$ at 38 mmHG and pO$_2$ at 85 mmHg. Direct arterial blood pressure was measured from the right common carotid artery. The test compounds were administered through a canula placed in the marginal ear vein. Each foreleg was taped to a cushioned plate held in a femur clamp attached to the spinal board rack. The left centeral digit of each paw was connected to a force displacement transducer for measurement of muscle tension. Nerve stimulation was provided by pairs of pin electrodes placed on both sides of the ulnar nerve at the elbow of both forearms. The right ulnar nerve was stimulated at Hz, 1 pps for 0.5 msec duration. The left ulnar nerve was similarly stimulated, every 15 seconds, with addition of interspersed trains-of-four and tetanizing stimuli. The parameters reported in Table II are:

potency (ED90), which is the dose required to depress twitch tension to 10% of its control value; onset (T85%), which is the time from injection unit 85% of the maximal drug effect is achieved, duration, which is the time from injection until the train-of-four has recovered to 75%, blood pressure (BP), which is the percentage change of pre-drug blood pressure; and heart rate (HR), which is the percentage change from pre-drug heart rate.

TABLE II

| Rabbit Paw Twitch Equi-efficacious Dose Data | | | | |
|---|---|---|---|---|
| Compound | ED90 (mg/kg) | T85% (seconds) | Duration (minutes) | BP (% change) | HR (% change) |
| atracurium | 0.05 | 126.90 | 14.30 | −3.40 | −1.00 |
| vecuronium | 0.02 | 97.30 | 16.80 | 1.10 | −1.90 |
| pancuronium | 0.02 | 147.50 | 32.50 | 2.70 | 0.00 |
| Compound C | 4.41 | 37.60 | 17.4 | −40.30 | −0.80 |
| compound D | 31.13 | 36.3 | 15.00 | −28.30 | 4.60 |

In Tables I and 11, the designated compounds are as follows:

Compound A—Me$_3$N$^+$-Phe-NH-(CH$_2$)$_6$-NH-Phe-N$^+$Me$_3$2I$^-$

Compound B—Me$_3$N$^+$-Leu-Phe-Leu-NH-(CH$_2$)$_5$-N$^+$Me$_3$2(CF$_3$CO$_2$)$^=$ Compound C—Me$_3$N$^+$-Phe-NH-(CH$_2$)$_{10}$-NH-Phe-N$^+$Me$_3$2I$^-$ Compound D—Me$_3$N$^+$-Phe-Leu-NH-(CH$_2$)$_2$-N$^+$Me$_3$2(CF$_3$CO$_2$)$^=$ Compound E—Me$_3$N$^+$-Leu-Phe-Leu-NH-(CH$_2$)$_7$-N$^+$Me$_3$2(CF$_3$CO$_2$)$^=$ The results in the Tables show that the subject compounds, while not as potent as those utilized for comparison, are advantageous in that they have a significantly shorter onset of activity.

We claim:

1. A peptide amide or amide dimer compound selected from those represented by the formulae:

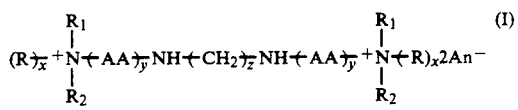

and

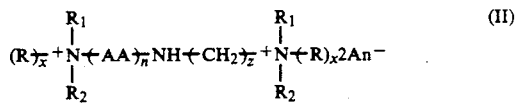

wherein
R is methyl or ethyl;
R$_1$ and R$_2$ are independently selected from the group consisting of methyl, ethyl and allyl, or R and one or both of R$_1$ and R$_2$, together with the nitrogen to which they are attached, form a heterocyclic ring selected from the group consisting of pyrrolidine, piperidine, piperazine and hexamethyleneimine;
AA are independently selected from the group consisting of Ala, Val, Leu, Ile, Phe and Pro;
n is 2 to 4;
x is independently 0 or 1;
y is independently 1 or 2;
z is 2 to 12; and
An$^-$ is a pharmaceutically acceptable anion.

2. A compound in accordance with claim 1, wherein said compound is selected from those represented by the formula:

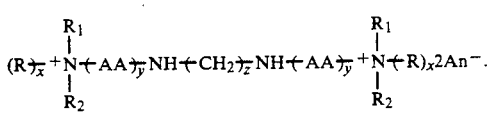 (I)

3. A compound in accordance with claim 1, wherein said compound is selected from those represented by the formula:

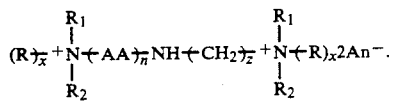 (II)

4. A compound in accordance with claim 1, wherein said compound $Me_3N^+$-Phe-NH-$(CH_2)_{10}$-NH-Phe-$N^+Me_3 2An^-$.

5. A compound in accordance with claim 1, wherein said compound $Me_3N^+$-Phe-NH-$(CH_2)_{12}$-NH-Phe-$N^+Me_3 2An^-$.

6. A compound in accordance with claim 1, wherein said compound $Me_3N^+$-Phe-Leu-NH-$(CH_2)_7$-$N^+Me_3$-$2An^-$.

7. A compound in accordance with claim 1, wherein said compound $Me_3N^+$-Leu-Phe-Leu-NH-$(CH_2)_7$-$N^+Me_3 2An^-$.

8. A method of producing muscle relaxation in a mammal comprising administering to said mammal an effective amount of peptide amide or an amide dimer in accordance with claim 1.

9. A method in accordance with claim 8, wherein said compound is selected from those represented by the formula:

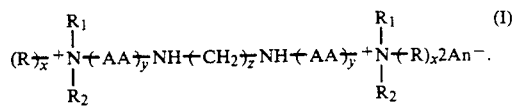 (I)

10. A method in accordance with claim 8, wherein said compound is selected from those represented by the formula:

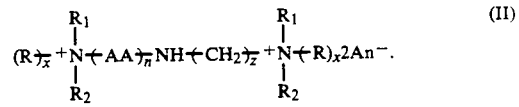 (II)

11. A muscle relaxant composition comprising a pharmaceutically acceptable vehicle for parenteral administration and a peptide diamide or amide dimer in accordance with claim 1.

12. A composition in accordance with claim 11, wherein said compound is selected from those represented by the formula:

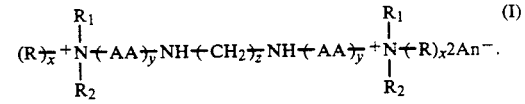 (I)

13. A composition in accordance with claim 11, wherein said compound is selected from those represented by the formula:

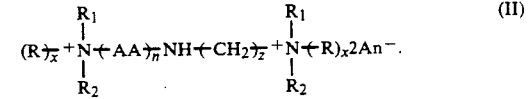 (II)

* * * * *